United States Patent [19]

Boddie

[11] 4,192,302

[45] Mar. 11, 1980

[54] HEPATIC ISOLATION AND PERFUSION CIRCUIT ASSEMBLY

[76] Inventor: Arthur W. Boddie, 110 Chimney Rock, San Antonio, Tex. 78231

[21] Appl. No.: 941,715

[22] Filed: Sep. 12, 1978

[51] Int. Cl.² ............................................. E03D 9/04
[52] U.S. Cl. ............................ 128/214 R; 128/214 B; 128/1 R; 128/DIG. 3
[58] Field of Search ......... 128/214 R, 214 B, DIG. 3, 128/1 R; 422/45; 210/321

[56] References Cited

U.S. PATENT DOCUMENTS

| | | | |
|---|---|---|---|
| 2,587,910 | 3/1952 | Shulman | 3/1 X |
| 3,483,867 | 12/1969 | Markovitz | 128/214 R |
| 3,490,438 | 1/1970 | Lavender et al. | 128/214 R |
| 3,516,408 | 6/1970 | Montanti | 128/334 C |
| 3,533,408 | 10/1970 | Paoli | 128/214 R |
| 3,638,649 | 2/1972 | Ersak | 128/214 R |
| 3,881,483 | 5/1975 | Sausse | 128/214 R |
| 3,890,969 | 6/1975 | Fischel | 128/214 R |
| 3,946,731 | 3/1976 | Lichtenstein | 128/DIG. 3 |
| 4,061,141 | 12/1977 | Hyden et al. | 128/214 R |

OTHER PUBLICATIONS

Article–"Isolated Perfusion of the Liver with HN₂" Ausman and Aust, Surgical Forum, 1960, vol. X, pp. 77–79.
Article–Development of a Technic for Isolated Perfusion of the Liver", Ausman, *N.Y. State Medical Journal*, 1961, pp. 3993–3997.
Article–"A Technique of Isolated Perfusion of the Liver", Chung, et al. *Surgery*, 1962, vol. 51, No. 4, pp. 508–511.

*Primary Examiner*—Henry K. Artis
*Attorney, Agent, or Firm*—Joseph E. Rusz; Arsen Tashjian

[57] ABSTRACT

The assembly, through a plurality of shunts, allows blood circulation from the lower part of a patient's body and from the intestines to flow unimpeded to the heart, while isolating hepatic venous blood containing toxic agents from the general circulation and returning it to a heart-lung machine. As a result, the assembly can be used to perfuse the liver, of a patient which has become involved with cancer, with extremely high does of cancericidal chemotherapy agents, while at the same time avoiding the toxic effects of these agents on the patient's body as a whole.

5 Claims, 3 Drawing Figures

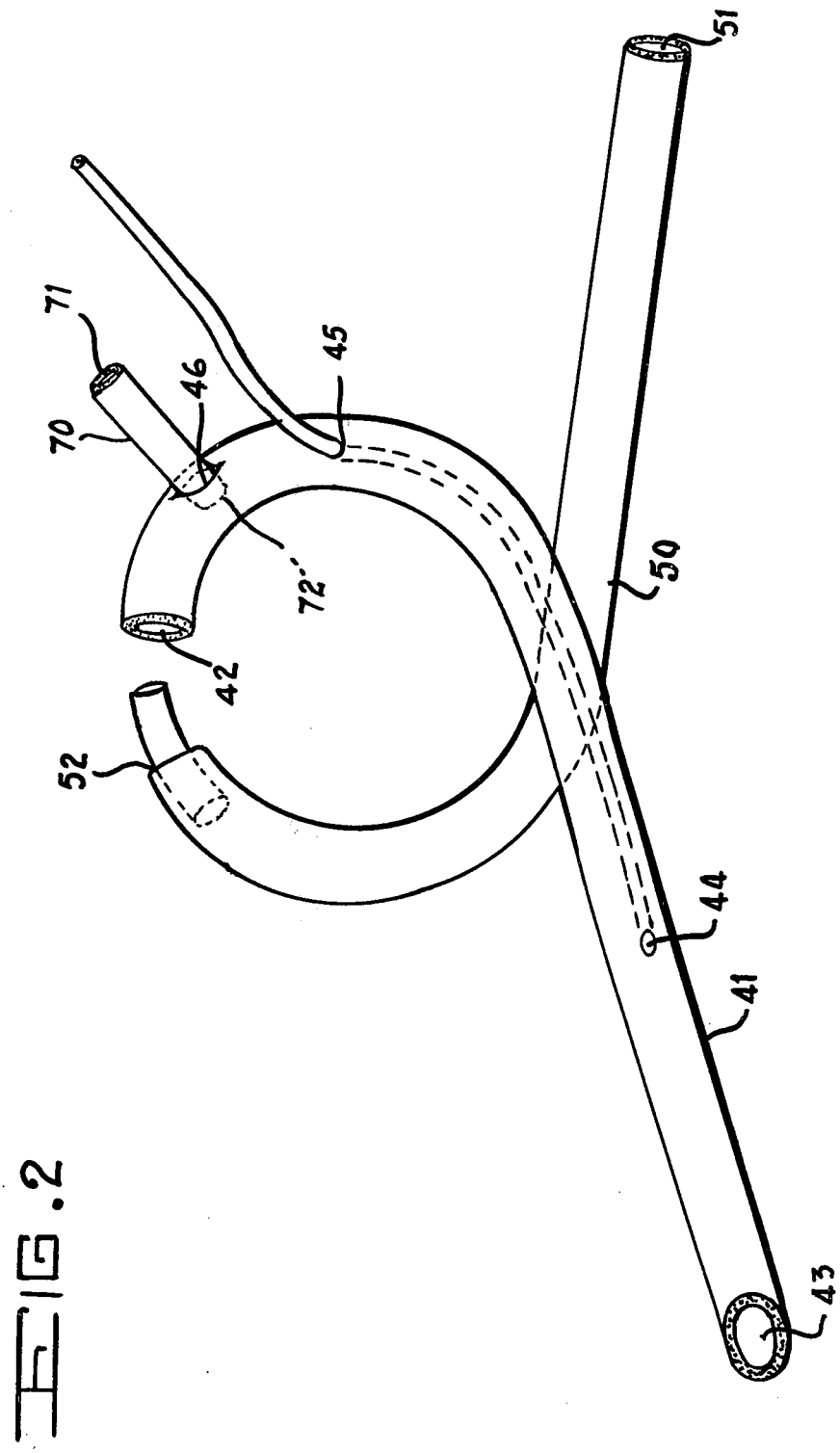

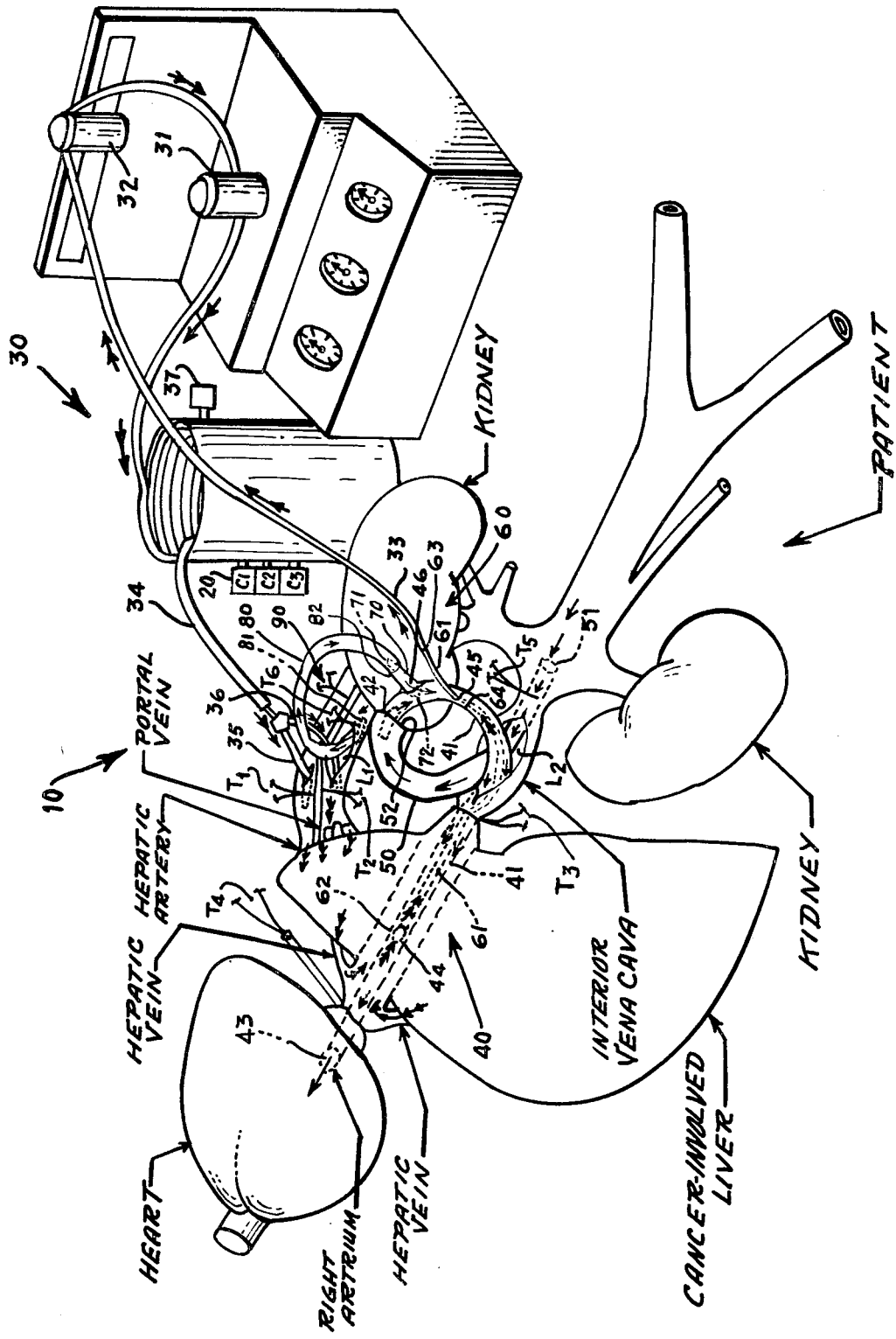

HEPATIC ISOLATION AND PERFUSION CIRCUIT ASSEMBLY

STATEMENT OF GOVERNMENT INTEREST

The invention described herein may be manufactured and used by or for the Government for governmental purposes without the payment of any royalty thereon.

BACKGROUND OF THE INVENTION

This invention relates to a hepatic isolation and perfusion circuit assembly and, more particularly, to a blood circuit for isolating the liver's blood circulation from the blood circulation of the rest of the body, and connecting the liver's circulation to a heart-lung machine and a source of cancericidal chemotherapy agents, thereby permitting perfusion of the liver (of a patient which has become involved with cancer) with extremely high doses of the chemotherapy agents, and yet at the same time avoiding the toxic effects of these agents on the body as a whole.

At present there is no effective means of treating patients with primary or metastatic cancer involving the liver. As a result, approximately 10,000–15,000 human patients die yearly with primary liver cancer or isolated hepatic metastases.

My inventive circuit will allow cancericidal doses of drugs to be delivered to liver cancers without undue general toxic effects to the patient and, thereby, prolonging the life and the quality of life of the patient.

I have, thereby, significantly advanced the state-of-the-art.

SUMMARY OF THE INVENTION

This invention pertains to the medical art and, more specifically, to a novel hepatic isolation and perfusion circuit assembly for use in treating a patient with a cancer-involved liver by delivering cancericidal chemotherapy agents to his liver without toxic effects to the body of the patient as a whole.

Accordingly, the principal object of this invention is to teach the structure of a preferred embodiment of my unique circuit assembly.

This principal object, as well as other related objects, of my invention will become readily apparent after a consideration of the description of the invention, together with reference to the Figures of the drawing.

DESCRIPTION OF THE DRAWINGS

FIG. 2 is a pictorial representation, in simplified form, of some of the major members of the means component, of my inventive circuit assembly, for selectively isolating a patient's cancer-involved liver, and the blood circulating therein, from his general blood circulatory system; and FIG. 3 is a representation, partially pictorial and partially schematic, and in simplified form, of a preferred embodiment of my invention circuit assembly in use in its working environment.

DESCRIPTION OF THE PREFERRED EMBODIMENT

Figure 1:
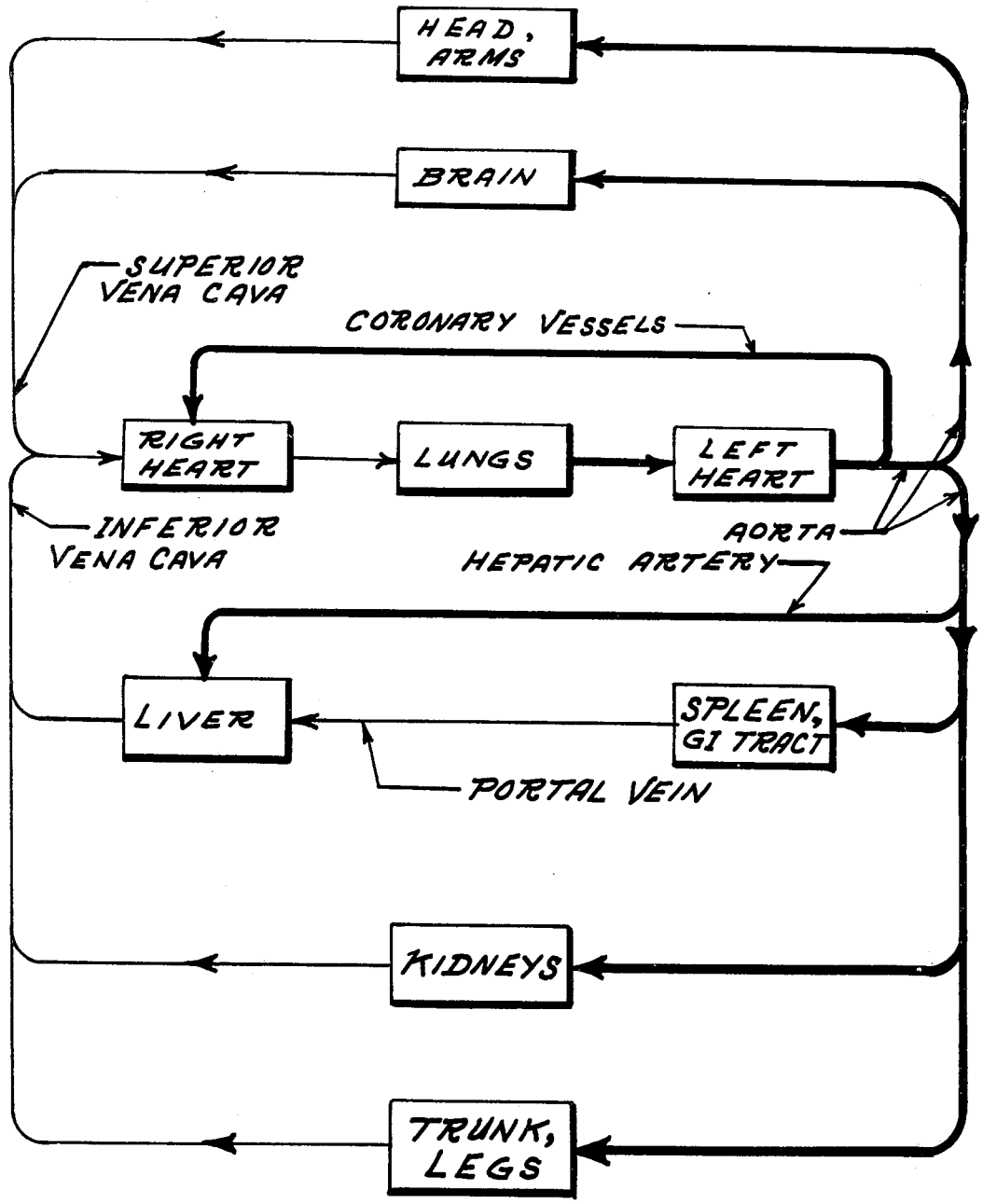
FIG. 1 is a representation, in simplified schematic form, of the blood circulatory system of a normal human.

With reference to FIG. 3, therein is shown the preferred embodiment 10 of my invention. It is here to be noted, with reference to FIGS. 1 and 3, that my invention is for use in treating a patient (such as is schematically represented in FIG. 1, and is pictorially represented in FIG. 3) having a body with a lower part (i.e., legs, trunk, and the like), a heart with a right atrium, a portal vein, a hepatic artery, intestines (i.e., GI tract, spleen, and the like) kidneys, a liver involved with cancer, blood in the general blood circulatory system (the flow of which is indicated by single headed arrows), with a portion of this blood circulating in and through the cancer-involved liver (the flow of which is indicated by double-headed arrows), all of which are designated by appropriate legends.

Now, with reference to FIGS. 1–3, inclusive, in its most basic and generic form my inventive hepatic isolation and perfusion circuit assembly 10, comprises: a source 20 of a plurality of cancericidal chemotherapy agents (such as C1, C2 and C3, FIG. 3) for perfusing the cancer-involved liver; a heart-lung machine 30 (sometimes referred to as a "pump-oxgenator") that is readily commercially available, operatively connected to the source of the cancericidal chemotherapy agents 20, with the heart-lung machine 30 including pumps (such as 31 and 32), an inlet 33, an outlet 34 that is bifurcated into a first branch catheter 35 and a second branch catheter 36, and a source of oxygen 37, and where the first branch catheter 35 is removably inserted into, is conformably engaged with, and is releasably secured to the hepatic artery, and where the second branch catheter 36 is removably inserted into, is conformably engaged with, and is releasably secured to a preselected location L1 at end in the portal vein; and, means (generally designated 40) for selectively isolating the patient's cancer-involved liver, and the blood circulating therein, from the general circulatory system of the patient, with this means 40 releasably connected to the heart-lung machine 30.

More specifically, this means 40 is a subassembly and comprises: a first catheter 41, FIGS. 2 and 3, having an inlet 42, an outlet 43, a first opening 44, a second opening 45, and a third opening 46, with the outlet 43 removably inserted into, conformably engaged with, and releasably secured to the inferior vena cava at a location L2 intermediate the liver and the kidneys, and with the outlet 43 simultaneously positioned in, and in communication with, the right atrium of the patient's heart, and with the inlet 42 protruding from the inferior vena cava; a second catheter 50 having an inlet 51 and an outlet 52, with the inlet 51 removably inserted into, conformably engaged with, and releasably secured to, the inferior vena cava at the same location (i.e., L2) as the first catheter 41, and directionally oppositely disposed with relation to the outlet 43 of the first catheter 41, and with the outlet 52 of this second catheter 50 protruding from the inferior vena cava and releasably connected to the inlet 42 of the first catheter 41, whereby a loop is formed external of the inferior vena cava; a hepatic venous return line 60 comprising a tube 61 having an inlet 62, an outlet 63, and a portion 64 intermediate the inlet 62, and the outlet 63, with this line 60 (and, more definitively, the tube 61) passing into the first catheter 41 through second opening 45 of that catheter 41, and with the inlet 62 of the tube 61 positioned internally of the first catheter 41 and in sealing communication with the first opening 44 of the first catheter 41, and with the intermediate portion 64 of the tube 61 positioned at, and conformably engaging with, the second opening 45 of the first catheter 41, and further with the outlet 63 of the tube 61 positioned externally of the first catheter 41 and releasably connected to the inlet 33 of the heart-lung machine 30; a portal shunt side arm 70, FIGS. 2 and 3 passing through, and conformably engaging with, the third opening 46 of the first catheter 41, with this shunt side arm 70 having an outlet 71 positioned internally of the first catheter 41, and an inlet 72 positioned externally of the first catheter 41; a third catheter 80 having an inlet 81 and an outlet 82, with the outlet 82 releasably connected to the inlet 71 of the portal shunt side arm 70, and with the inlet 81 removably inserted into, conformably engaged with, and releasably secured to the portal vein at the same location (i.e., L1) as the second branch catheter 36 of the bifurcated outlet 34 of the heart-lung machine 30, and directionally oppositely disposed with relation to the second branch catheter 36; and, means (generally designated 90) for occluding blood from flowing into the liver from the hepatic artery, with this means 90 disposed upstream of the location of the first branch catheter 35 in the hepatic artery.

As a matter of preference, and not of limitation, the first catheter 41, the second catheter 50, the third catheter 80, the hepatic venus return line 60, the first branch catheter 35 of the outlet 34 of the heart-lung machine 30, and the second branch catheter 36 of the outlet 34 of the heart-lung machine 30 are made of flexible material.

Additionally, as a matter of preference, and also not as a matter of limitation, ligatures (such as T1–T6, inclusive) are used to conformably engage and releasably hold: the first branch catheter 35 to the hepatic artery (i.e., T1), the second branch catheter 36 to the portal vein (i.e., T2); the outlet 43 of the first catheter 41 to the inferior vena cava (i.e., T3); the outlet 43 of the first catheter 41 to the right atrium (i.e., T-4); the inlet 51 of the second catheter 50 to the inferior vena cava (i.e., T5); and, the inlet 81 of the third catheter 80 to the portal vein (i.e., T6).

Further, the means 90 for occluding blood flowing into the liver from the hepatic artery also preferably is a ligature.

MANNER OF OPERATION AND OF USE OF THE PREFERRED EMBODIMENT

The manner of operation and of use of the preferred embodiment 10, FIGS. 2 and 3, of my invention hepatic isolation and perfusion circuit can be easily ascertained by any person of ordinary skill in the art from the foregoing description, coupled with reference to the Figures of the drawings.

For others, it is sufficient to say that, if one follows the route of the blood flow that is designated by single-headed arrows in FIG. 3 (i.e., the blood that is flowing in the general circulatory system), and compares it with the route of the blood flow that is designated by double-headed arrows in FIG. 3 (i.e., the blood flow that is limited to and from the cancer-involved liver by the use of my invention), then one can readily see how my invention structurally and successfully accomplishes the functions of selectively isolating the liver's blood circulation from the blood circulation of the rest of the body, and of connecting the liver's isolated circulation to the heart-lung machine 30, FIG. 3, and to the source of cancericidal chemotherapy agents C1–C3, inclusive, FIG. 3, and thereby permitting the perfusion only of the liver.

CONCLUSION

It is abundantly clear from all of the foregoing, and from the Figures of the drawings, that the stated principal object, and other related objects, of my invention have been achieved.

It is to be noted that, although there have been described the fundamental and unique features of my invention as applied to a preferred embodiment, various other embodiments, variations, adaptations, substitutions, additions, omissions, and the like may occur to, and can be made by, those of ordinary skill in the art, without departing from the spirit of my invention.

What is claimed is:

1. A hepatic isolation and perfusion circuit assembly, for use in treating a patient having a body with a lower part, a heart with a right atrium, a portal vein, a hepatic artery, intestines, kidneys, a liver involved with cancer, blood in a blood general circulatory system, with a portion of said blood circulating in and through said cancer-involved liver, wherein said blood circulating in said liver includes a hepatic venous outflow, comprising:
    a. a source of a plurality of cancericidal chemotherapy agents for perfusing said cancer-involved liver;
    b. a heart-lung machine, operatively connected to said source of said cancericidal chemotherapy agents, wherein said machine includes an inlet, an outlet that is bifurcated into a first branch catheter and a second branch catheter, and a source of oxygen, and wherein said first branch catheter of said bifurcated outlet is removably inserted into, is conformably engaged with, and is releasably secured to said hepatic artery of said patient, and also wherein said second branch catheter of said bifurcated outlet is removably inserted into, is conformably engaged with, and is releasably secured to a preselected location at and in said portal vein of said patient;
    c. and, means for selectively isolating said patient's cancer-involved liver, and said blood that is circulating therein, from said general blood circulatory system of said patient, with this said means releasably connected to said heart-lung machine;
    whereby said blood circulating in and through said cancer-involved liver can be oxygenated in and by said heart-lung machine, and whereby each of said plurality of cancericidal chemotherapy agents can be introduced from said source selectively into and added to said oxygenated blood, thereby permitting and causing said cancer-involved liver of said patient to be perfused with any of said cancericidal chemotherapy agents, and whereby, simultaneously, said blood circulating from said lower part of said patient's body and from said intestines of said patient is allowed to continue to flow and to circulate unimpeded to said patient's heart.

2. A hepatic isolation and perfusion circuit assembly, as set forth in claim 1, wherein said means for selectively isolating said blood that is circulating in and through said cancer-involved liver from the said general blood circulatory system includes a hepatic perfusion catheter subassembly which comprises:
    a. a first catheter having an inlet, an outlet, a first opening, a second opening, and a third opening, with said outlet removably inserted into, conformably engaged with, and releasably secured to said inferior vena cava of said patient at a location intermediate said liver and said kidneys of said patient, and with said outlet positioned in, and in communication with, said right atrium of said heart of said patient, and with said inlet protruding from said inferior vena cava;

b. a second catheter having an inlet and outlet, with said inlet removably inserted into, conformably engaged with, and releasably secured to said inferior vena cava of said patient at said same location as said first catheter and directionally oppositely disposed with relation to said outlet of said first catheter, and with said outlet of this second catheter protruding from said inferior vena cava and releasably connected to said inlet of said first catheter, whereby a loop is formed external of said inferior vena cava;

c. a hepatic venous return line comprising a tube having an inlet, an outlet, and a portion intermediate said inlet and said outlet, with this said line passing into said first catheter through said second opening of said first catheter, and with said inlet of said line positioned internally of said first catheter and in sealing communication with said first opening of said first catheter, and also with said intermediate portion positioned at, and conformally engaged with, said second opening of said first catheter, and further with said outlet of this said line positioned externally of said first catheter and releasably connected to said inlet of said heart-lung machine;

d. a portal shunt side arm passing through, and conformably engaging with, said third opening of said first catheter, with this said portal shunt side arm having an outlet positioned internally of said first catheter, and an inlet positioned externally of said first catheter;

e. a third catheter having an inlet and an outlet, with said outlet releasably connected to said inlet of said portal shunt side arm, and with said inlet removably inserted into, conformably engaged with, and releasably secured to said portal vein of said patient at said same location as said second branch catheter of said bifurcated outlet of said heart-lung machine and directionally oppositely disposed with relation thereto;

f. and, means for occluding blood from flowing into said liver from said hepatic artery, with said means disposed upstream of said location of said first branch catheter, of said outlet of said heart-lung machine, in said hepatic artery;

whereby said hepatic venous outflow is prevented from entering said heart of said patient, and is isolated from said general blood circulatory system, and thereby is diverted and is shunted to said heart-lung machine and to said source of cancericidal chemotherapy agents and, thereafter, is conducted to, and is perfused through, said cancer-involved liver of said patient through said hepatic artery.

3. A hepatic isolation and perfusion circuit assembly, as set forth in claim 2, wherein said first catheter, said second catheter, said third catheter, said hepatic venus return live, said first branch catheter of said outlet of said heart-lung machine, and said second branch catheter of said outlet of said heart-lung machine are all made of flexible material.

4. A hepatic isolation and perfusion circuit assembly, as set forth in claim 3, wherein ligatures are used to conformably engage and releasably hold: said first branch catheter of said outlet of said heart-lung machine to said hepatic artery of said patient; said second branch catheter of said outlet of said heart-lung machine to said portal vein of said patient; said outlet of said first catheter to said inferior vena cava of said patient; said outlet of said first catheter to said right atrium of said heart of said patient; said inlet of said second catheter to said inferior vena cava of said patient; and, said inlet of said third catheter to said portal vein of said patient.

5. A hepatic isolation and perfusion circuit, as set forth in claim 4, wherein said means for occluding blood flowing into said liver from said hepatic artery is a ligature.

* * * * *